(12) United States Patent
Hasegawa et al.

(10) Patent No.: US 6,497,839 B1
(45) Date of Patent: Dec. 24, 2002

(54) STERILIZER AND STERILIZATION METHOD UTILIZING HIGH VOLTAGE

(75) Inventors: Hideo Hasegawa; Koji Takeda; Homare Aman; Toshiyuki Tamura, all of Osaka-fu (JP)

(73) Assignee: Sanyo Electric Co., Ltd., Osaka-fu (JP)

( * ) Notice: Subject to any disclaimer, the term of this patent is extended or adjusted under 35 U.S.C. 154(b) by 0 days.

(21) Appl. No.: 09/679,010

(22) Filed: Oct. 4, 2000

(51) Int. Cl.$^7$ ................................................. A61L 2/20
(52) U.S. Cl. ......................... 422/22; 422/3; 422/29; 422/186.03
(58) Field of Search ................ 422/22.3, 186.03, 422/29; 55/138; 204/156

(56) References Cited

U.S. PATENT DOCUMENTS

| | | | | |
|---|---|---|---|---|
| 4,216,000 A | * | 8/1980 | Kofoid | 55/138 |
| 5,549,041 A | * | 8/1996 | Zhang et al. | 99/451 |
| 5,603,893 A | * | 2/1997 | Gundersen et al. | 422/22 |
| 6,059,935 A | * | 5/2000 | Spence | 204/156 |
| 6,103,190 A | * | 8/2000 | Tanimura et al. | 422/29 |

FOREIGN PATENT DOCUMENTS

JP 63-50984 10/1988

* cited by examiner

Primary Examiner—Robert J. Warden, Sr.
Assistant Examiner—Sean E. Conley
(74) Attorney, Agent, or Firm—Weingarten, Schurgin, Gagnebin & Lebovici LLP

(57) ABSTRACT

A sterilizer and a sterilization method: which can easily and efficiently sterilize various kinds of bacteria at a room temperature and an atmospheric pressure so as to reduce the number of bacteria, without deteriorating qualities inherent to a sterilization object; which does not require pretreatment and/or after-treatment; which is highly safe; and which does not cause the ozone layer depletion problem. In a sterilizer comprising a power supply section for generating a high voltage and a processing device having a discharge side electrode and a ground side electrode to which the generated high voltage is applied, sterilization is performed by interposing a sterilization object between the electrodes and by causing a pulse streamer discharge between the electrodes at a room temperature and an atmospheric pressure and in the atmosphere in which a humidity is controlled to be suitable for sterilization.

8 Claims, 10 Drawing Sheets

Fig. 11
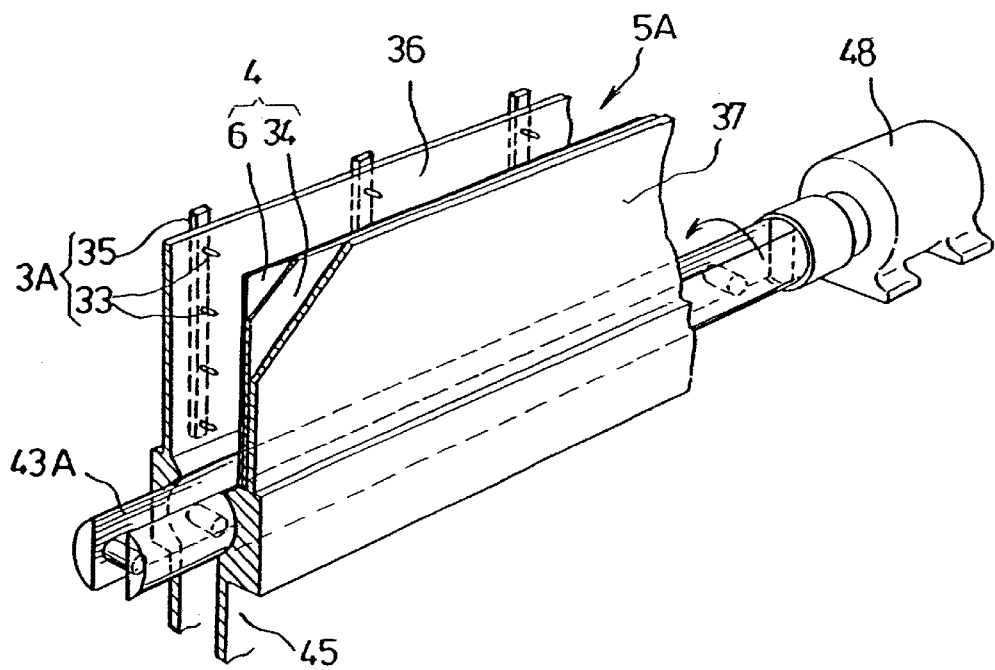
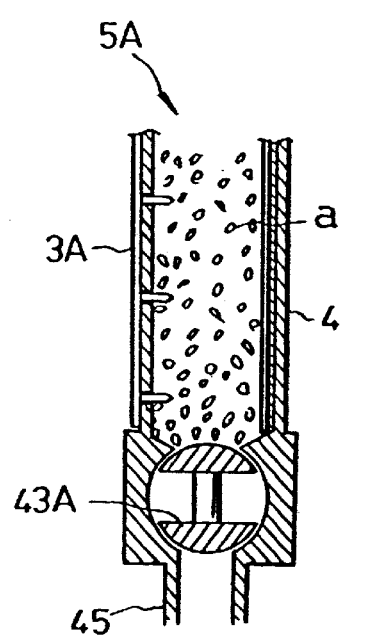
Fig. 12 A
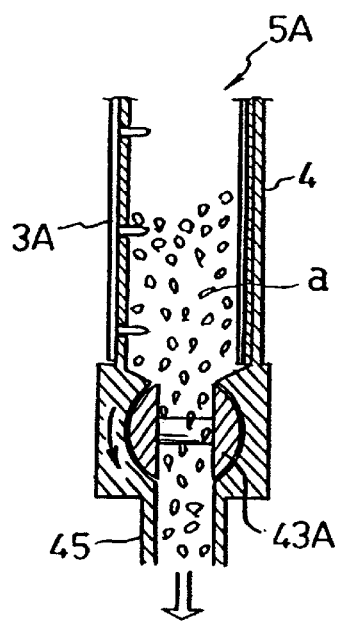
Fig. 12 B

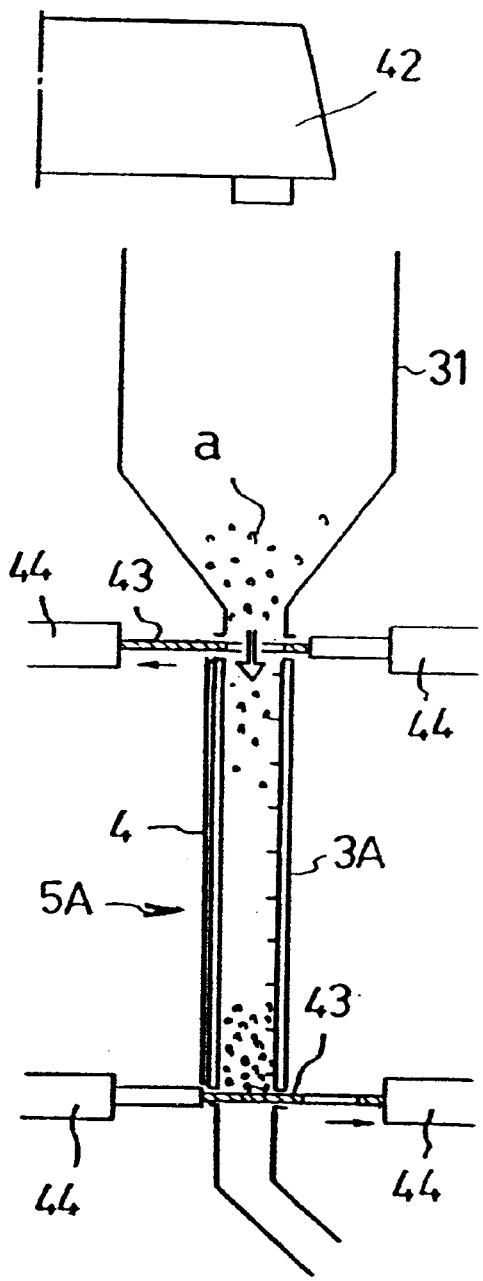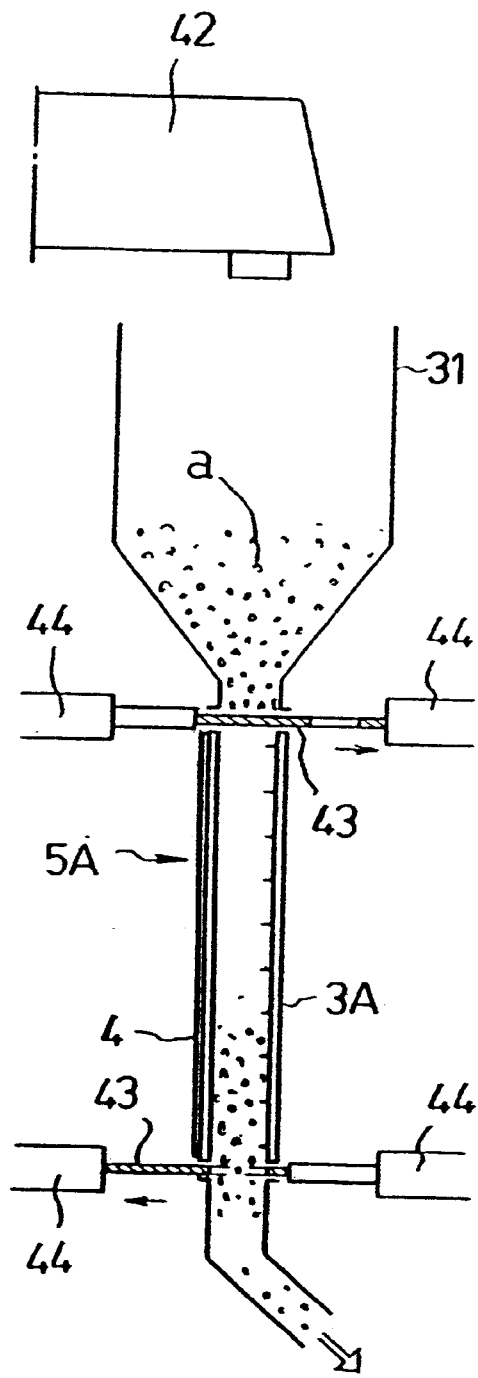
Fig. 13 A
Fig. 13 B

STERILIZER AND STERILIZATION METHOD UTILIZING HIGH VOLTAGE

BACKGROUND OF THE INVENTION

1. Field of the Invention

The present invention relates to a sterilizer and a sterilization method which utilize a high voltage. More particularly, the present invention relates to a sterilizer utilizing a high voltage which can be used for solid products in general, e.g., foods, drugs, Chinese herb medicines, cosmetics, feedstuffs, and fertilizers, and in particular, which can be optimally used for foods unsuitable for being subjected to heating; and a sterilization method utilizing such a sterilizer.

2. Detailed Description of the Prior Art

Conventionally, heat sterilization has been generally employed as a method for sterilizing foods. Heat sterilization, however, causes changes in components, aromas, flavors, colors, etc., the escaping of active ingredients, and the like, thereby deteriorating the qualities of foods.

A method for sterilizing a food by bringing the food into contact with heated water vapor (Japanese Patent Publication No. 63-50984) has been suggested. Where this method is employed, however, changes and deterioration in a food quality are likely to occur because of the loss of an aroma component, the penetration of a water vapor into the food, and the like.

Methyl bromide fumigation has been conducted in order to sterilize rice and kill insects in rice. However, methyl bromide is designated as a dangerous substance due to its high inflammability. Methyl bromide is also designated as a deleterious substance, and a blister is formed when one's skin touches methyl bromide. Therefore, this method lucks in safety. In addition, when methyl bromide is released into the atmosphere and reaches the ozone layer around the globe, methyl bromide depletes the ozone layer due to its high potential to deplete the ozone layer.

Although ozone has been used for sterilization, the obtained sterilization effect is not sufficient. Also, in order to suppress an increase in the number of molds, low temperature storage (e.g., 15° C., 70–75% RH) has been conducted, long-term low temperature storage may cause an increase in the number of molds.

Radiation sterilization which utilizes cobalt-60 or the like is permitted to be used for adzuki bean, corn, spices, and the like. However, such a method requires a large equipment, and thus the equipment cost is high. In addition, shielding is required in order to prevent radiation from leaking to the outside.

If the number of microorganisms, in particular, the number of molds is increased during the storage of unpolished rice, for example, in the worst case scenario, the commercial value of the unpolished rice is lost, and the rice is no longer suitable for eating. It cannot be expected that spore forming bacteria attached to the rice will become extinct even at the time of cooking the rice.

Some foods are not suitable for being subjected to heat sterilization. For example, rice which is a staple food for Japanese people is not suitable for being subjected to heat sterilization or chemical treatments.

SUMMARY OF THE INVENTION

The first object of the present invention is to provide a sterilizer: which can easily and efficiently sterilize various kinds of bacteria, including spore forming bacteria attached to rice, at a room temperature and an atmospheric pressure so as to reduce the number of bacteria, without deteriorating qualities of a flavor, a taste, a beneficial effect, a power, dispersibility, and the like, which are inherent to an object to be sterilized (hereinafter, referred to as "sterilization object") such as a food, a drug, a Chinese herb medicine, a cosmetic, a feedstuff, and a fertilizer; which does not require pretreatment and/or after-treatment; which is highly safe; and which does not cause the ozone layer depletion problem The second object of the present invention is to provide a sterilization method which can easily, economically and efficiently sterilize various kinds of bacteria, including spore forming bacteria attached to rice, at a room temperature and an atmospheric pressure so as to reduce the number of bacteria by using the above-described sterilizer, without deteriorating qualities of a flavor, a taste, a beneficial effect, a power, dispersibility, and the like, which are inherent to a sterilization object such as a food, a drug, a Chinese herb medicine, a cosmetic, a feedstuff, and a fertilizer.

The inventors of the present invention conducted in-depth studies in order to solve the conventional problems. Consequently, they found that various kinds of bacteria including spore forming bacteria can be sterilized easily, efficiently, and economically by interposing a sterilization object between a discharge side electrode and a ground side electrode to which a high AC voltage or a pulsed high voltage is applied and by causing a pulse streamer discharge between the above-described electrodes at a room temperature and an atmospheric pressure in the atmosphere controlled to have a humidity suitable for sterilization, thereby completing the present invention.

In order to solve the above-described problems, the present invention according to claim 1 is a sterilizer which comprises: a power supply section for generating a high voltage; a processing device having a discharge side electrode and a ground side electrode to which the generated high voltage is applied; and humidity control means for controlling a humidity in the processing device. A sterilization object is interposed between the electrodes of the processing device, and a pulse streamer discharge occurs between the electrodes.

According to the present invention, various kinds of bacteria are sterilized by causing a pulse streamer discharge between the above-described electrodes.

While a corona discharge during the application of a DC voltage causes only the vicinity of the discharge side electrode to emit light, a pulse streamer discharge can excite a much wider area into a plasma state. The reasons for this are as follows. First, a pulse streamer discharge can instantaneously apply a voltage higher than a spark voltage in the case of a DC corona discharge, thereby broadening the high electric field region. Second, while a discharge is suppressed in the case of a DC corona discharge because of a reduced electric field strength in an ionization region near the discharge side electrode due to ionic space charge, discharge suppression due to a space charge electric field is very small in the case of a pulse streamer discharge because of the rapid start-up of the voltage.

The present invention according to claim 2 is characterized in that the discharge side electrode comprises a large number of needle-shaped electrodes which are provided with a predetermined distance apart from one another in the sterilizer according to claim 1.

If plate-shaped electrodes are respectively used as the discharge side electrode and the ground side electrode, the surface areas thereof are increased. Thus, there is a need to increase the capacity of a power supply section for generating a high voltage. Also, both of the plate-shaped electrodes need to be absolutely parallel to each other. If the parallel state is not maintained, a discharge occurs only in a certain area. In the case where a needle-shaped electrode is used as the discharge side electrode and a plate-shaped electrode is used as the ground side electrode, wide-ranging sterilization of sterilization objects interposed between the aforementioned electrodes cannot be achieved, resulting in uneven sterilization. If a large number of needle-shaped electrodes which are disposed with a predetermined distance apart from one another are used, a uniform discharge occurs and wade-ranging and uniform sterilization of sterilization objects interposed between the electrodes can be thereby achieved. Thus, uneven sterilization does not occur.

In order to prevent rusting and to provide durability, the needle-shaped electrode may be preferably made of a material such as a stainless material, a platinum material, or the like. Preferably, the tip of the stainless needle-shaped electrode may have a thickness of about 0.1 to 1 mm Ø. More preferably, the tip of the stainless needle-shaped electrode has a thickness as thin as about 0.1 to 0.5 mm Ø.

The distance between the needle-shaped electrodes is not limited to any particular value since the applied voltage, pulse number, input energy (cal/cm$^3$), electric field strength, and the like are varied depending on the kind and form of a sterilization object, the kind and form of a bacterium, and the like. It is preferred that the distance between the needle-shaped electrodes is suitably determined so that a sterilization object can be sufficiently and uniformly sterilized without deteriorating the qualities of a flavor, a taste, and the like, which are inherent thereto.

However, it is desirable that the aforementioned distance is selected generally from the range of 5 mm to less than 80 mm, preferably from the range of 10 mm to 60 mm, and most preferably from the range of 25 mm to 30 mm. If the distance is less than 5 mm, it is possible to sterilize unpolished rice. However, the capacity of a power supply which will be described later needs to be increased, and thus, such a distance selection is uneconomical. If the distance is 80 mm or greater, wide-ranging and uniform sterilization of sterilization objects which are interposed between the above-described electrodes cannot be achieved, resulting in uneven sterilization.

The present invention according to claim 3 is characterized in that the ground side electrode comprises a plate-shaped electrode whose entire surface is covered with an insulating plate in the sterilizer according to claim 1 or 2.

It is preferred to dispose an insulating plate on a surface of the ground side electrode opposing to the discharge side electrode so as to cover the entire surface thereof so that, in a pulse streamer discharge, a discharge from the needle-shaped electrode is not shorted to the junction. By disposing the insulating plate, a discharge occurs safely and uniformly, thereby making it possible to sterilize a sterilization object uniformly and efficiently.

The present invention according to claim 4 is characterized in that the insulating plate is a ceramic plate in the sterilizer according to claim 3.

An acrylic plate, a glass plate, or the like is generally employed as an insulating plate used for the above-described purpose due to its low price. However, an acrylic plate, a glass plate, or the like lacks in durability and strength. Therefore, when an applied voltage is increased, it is preferred to use a ceramic plate having high durability, strength, and insulating property. The ceramic plate may be a large single sheet of plate, or a 1×1 cm small thin plate with the thickness of 1 mm, for example. Small ceramic plates are cheap because they are mass-produced, and it is possible to use many small ceramic plates as a large ceramic plate by binding them with one another.

The present invention according to claim 5 is characterized in that the ceramic plate is a ceramic plate having a high withstand voltage in the sterilizer according to claim 4.

Specifically, an alumina plate, for example, may be preferably used as a ceramic plate with a high withstand voltage, and more preferably, a high purity alumina plate can be used.

The present invention according to claim 6 is characterized in that the processing device is made of a material having a volume resistivity in the range of $10^{10}$ to $10^{14} \Omega \cdot cm$ or more in the sterilizer according to any one of claims 1 to 5.

In order to sterilize a sterilization object safely, a processing device for sterilizing a sterilization object may be preferably made of a highly insulating material having a volume resistivity in the range of $10^{10} \sim 10^{14} \Omega \cdot cm$ or more. Specifically, such a material may be an electrical insulating material such as a polyolefin resin, an acrylic resin, a polycarbonate resin, various engineering plastics, or a FRP.

According to the present invention of claim 7, in a processing device having a discharge side electrode and a ground side electrode to which a high voltage generated in a power supply section for generating a high voltage is to be applied, a sterilization method comprises the steps of: interposing a sterilization object between the electrodes to which a high voltage is applied, and causing a pulse streamer discharge between the electrodes at a room temperature and an atmospheric pressure and in the atmosphere in which a humidity is controlled to be suitable for sterilization, thereby performing sterilization.

Various kinds of bacteria including spore forming bacteria can be sterilized easily, efficiently, and economically by interposing a sterilization object between the discharge side electrode and the ground side electrode and by causing a pulse streamer discharge between the above-described electrodes at a room temperature and an atmospheric pressure and in the atmosphere in which a humidity is controlled to be suitable for sterilization.

The humidity suitable for sterilization is not limited to any particular value since it varies depending on the kind and form of a sterilization object, the kind and form of a bacterium, and the like. It is preferable that the humidity is suitably determined so that a sterilization object can be sufficiently and uniformly sterilized without deteriorating the qualities of a flavor, a taste, and the like, which are inherent thereto.

The present invention according to claim 8 is characterized in that a pulsed high voltage of a positive polarity is applied to the discharge side electrode in the sterilization method according to claim 7.

If a pulsed high voltage of a negative polarity is applied to the discharge side electrode instead of applying a pulsed high voltage of a positive polarity thereto, dirt, dust, and the like may be attached to the discharge side electrode, possibly failing to obtain a uniform and stable discharge. Thus, applying a pulsed high voltage of a negative polarity to the discharge side electrode is not preferable.

The present invention according to claim 9 is characterized in that a pulsed high voltage with a start-up time of 10 nanoseconds or more and a duration of 1 microsecond or less is applied to the discharge side electrode in the sterilization method according to claim 7 or 8.

If a pulsed high voltage with a start-up time on the order of 10 nS (nanoseconds) or more and a duration of about 1 μS (microsecond) or less is applied to the discharge side electrode, a streamer discharge linearly extending from the discharge side electrode occurs. Thus, a wide area between the electrodes can be exited into a plasma state, and a sterilization object interposed between the electrodes can be uniformly sterilized.

The thus-structured sterilizer of the present invention has a simple structure, and can easily and efficiently sterilize a sterilization object at a room temperature and an atmospheric pressure and in the atmosphere in which a humidity is controlled without deteriorating the qualities inherent to the sterilization object. In addition, this sterilizer requires no pretreatment and/or after-treatment, is highly safe, and does not cause the ozone layer depletion problem Although a high voltage is used, the current value is very small. Therefore, this sterilizer is safe and requires a low energy. Since no chemicals are used and no heating is performed, changes hardly occur in the qualities of a sterilization object, and no chemicals or the like stay behind. Since the temperature of a sterilization object rarely rises, it is possible to sterilize a sterilization object which is not suitable for being subjected to heating.

According to the above-described sterilization method of the present invention, it is possible to easily, economically, and efficiently sterilize various kinds of bacteria, including spore forming bacteria attached to rice, at a room temperature and an atmospheric pressure and in the atmosphere in which a humidity is controlled so as to reduce the number of bacteria, without deteriorating qualities of a flavor, a taste, a beneficial effect, a power, dispersibility, and the like, which are inherent to a sterilization object such as a food, a drug, a Chinese herb medicine, a cosmetic, a feedstuff, and a fertilizer.

BRIEF DESCRIPTION OF THE DRAWINGS

These and other objects and advantages of the present invention will become clear from the following description with reference to the accompanying drawings, wherein:

FIG. 11 is a diagram for illustrating another example of a shutter capable of being opened and closed which is provided in a lower part of a processing device;

FIG. 12A is a diagram for illustrating a state in which the shutter shown in FIG. 11 is closed;

FIG. 12B is a diagram for illustrating a state in which the shutter shown in FIG. 11 is opened;

FIG. 13A is a diagram for illustrating a state in which unpolished rice in a hopper section is transferred to a processing tank while a shutter provided at a lower part of a sterilizer is closed and a shutter provided at a lower part of the hopper section is opened;

FIG. 13B is a diagram for illustrating a state in which sterilized unpolished rice is discharged to the outside by opening the shutter provided at the lower part of the processing device.

DETAILED DESCRIPTION OF THE PREFERRED EMBODIMENTS

One embodiment of the present invention will be described below with reference to the accompanying drawings.

Figure 1:
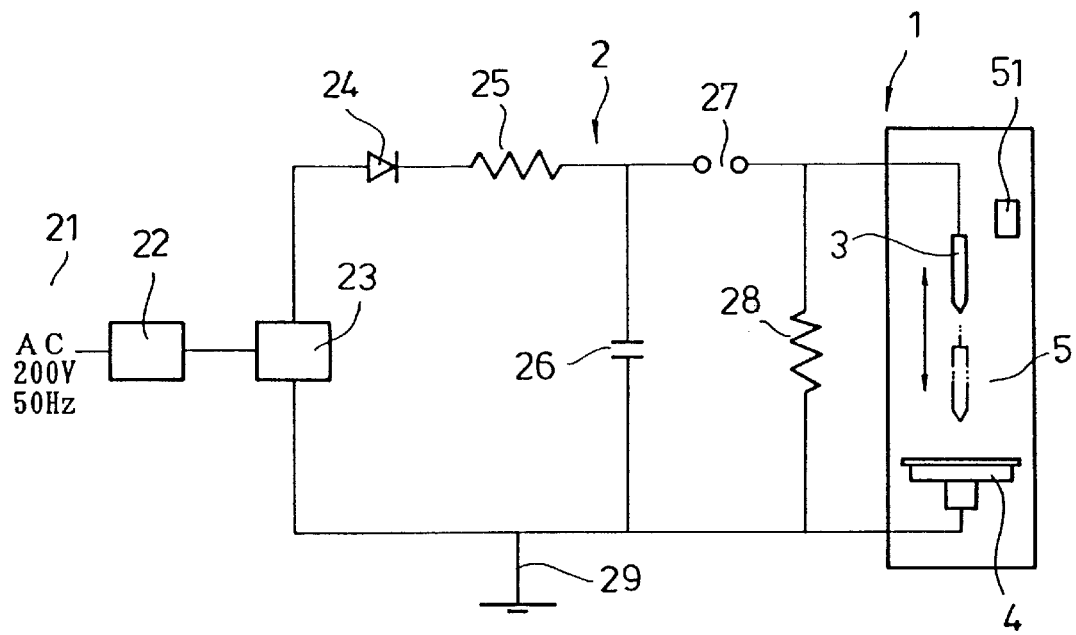
FIG. 1 is a diagram showing a general structure of a sterilizer of the present invention which utilizes a high voltage.

FIG. 1 is a diagram showing a general structure of a sterilizer utilizing a high voltage according to the present embodiment. In FIG. 1, a sterilizer 1 of the present invention comprises: a power supply section 2 for generating a high voltage; a processing device 5 having a discharge side electrode (e.g., a stainless electrode) 3 and a ground side electrode 4 to which the generated high voltage is applied; and humidity control means 51 for controlling a humidity in the processing device 5.

In the power supply section 2, a voltage input from a power supply 21 (AC 200 V, 50 Hz) is boosted by a slidac 22 and a high voltage transformer 23, and the voltage is rectified by a full-wave rectifier diode 24. Thereafter, the current value is lowered by a resistor 25, and a capacitor 26 is charged. The electric energy charged into the capacitor 26 is momentarily discharged through a gap 27, thereby being a pulsed voltage. The pulsed voltage is applied between the discharge side electrode 3 and the ground side electrode 4 of the processing device 5. Reference numeral 28 denotes a resistor, and reference numeral 29 denotes ground means.

Figure 2:
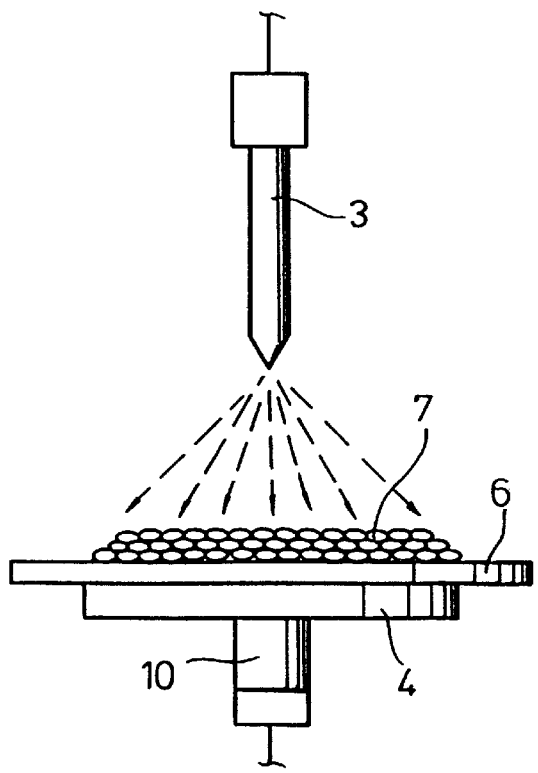
FIG. 2 is a diagram for illustrating a processing device of the sterilizer of the present invention shown in FIG. 1.

FIG. 2 is a diagram for illustrating the processing device 5 shown in FIG. 1. A ceramic plate ($Al_2O_3$) 6 as an insulating plate is disposed on the ground side electrode 4 in the processing device 5, and a sterilization object (e.g., unpolished rice) 7 is placed on the ceramic plate 6.

In the sterilizer 1 of the present invention, the sterilization object 7 is interposed between the discharge side electrode 3 and the ground side electrode 4 as described above, and the humidity control means 51 is actuated so as to control the atmosphere in the processing device 5 to have a humidity suitable for sterilization. The high voltage generated in the power supply section 2 becomes a pulsed voltage (e.g., a pulsed voltage which generates an energy wave about 100 times for one second), and the pulsed voltage is applied between the discharge side electrode 3 and the ground side electrode 4 of the processing device 5, thereby causing a pulse streamer discharge between the discharge side electrode 3 and the ground side electrode 4 at a room temperature and an atmospheric pressure. In this manner, sterilization is performed.

Since the shapes and sizes of the discharge side electrode 3 and the ground side electrode 4, applied voltage, pulse number, input energy (cal/cm$^3$), electric field strength, and the like are varied depending on the kind and form of a sterilization object, the kind and form of a bacterium, and the like, they are not limited to any particular shapes or values. It is preferable that they are suitably determined so that a sterilization object can be sufficiently sterilized without deteriorating the qualities of a flavor, a taste, a beneficial effect, a power, and a dispersibility, and the like, which are inherent to the sterilization object.

As specific examples of the shapes of the discharge side electrode 3 and the ground side electrode 4, the discharge side electrode 3 is a needle-shaped electrode, a bar-shaped electrode, or a plate-shaped electrode, and the ground side electrode 4 is a plate-shaped electrode.

In general, greater applied voltage, pulse number, input energy, and electric field strength result in more effective sterilization, and obtained sterilization is more effective when the applied voltage is higher than the pulse number. A higher electric field strength is more effective when input energies are the same.

Sterilization conditions such as a sterilization processing time in the processing device 5, a processing amount of sterilization objects, whether mixing is performed or not, and a humidity are varied depending on the kind and form of a sterilization object, the kind and form of a bacterium, and the like. Therefore, they are not Limited to any particular conditions, and it is preferable that they are suitably determined. However, a sterilization rate in the processing device 5 is affected particularly by a humidity. Therefore, it is possible to obtain a higher sterilization rate if a high humidity condition is employed.

Using the sterilizer 1 of the present invention shown in FIGS. 1 and 2, 30 g of unpolished rice (initial bacteria count: general live bacteria count is 8.2×105 cfu/g, fungi count (yeast, mold) is 3.5×105 cfu/g) was interposed between the discharge side electrode 3 and the ground side electrode 4 as a sterilzation object. Sterilization was performed at a room temperature (about 20° C.) and an atmospheric pressure with the applied voltage being 30 KV, the discharge current being about 0.01 to 0.1 Amp., and the sterilization processing time being 15 minutes. Under such conditions, sterilization was performed a plurality of times while varying a humidity in the processing tank 5 to be 30% RH or less, 30 to 50% RH, and 50% RH or more. Table 1 shows the results of measurements as to the general live bacteria count and fungi count (measurement by culturing) in the unpolished rice which has been sterilized in the respective humidities.

TABLE 1

|  | Initial bacterial count | Bacteria sterilization | count | after |
|---|---|---|---|---|
| Humidity (% RH) |  | 30 or less | 30–50 | 50 or more |
| General live bacteria count (cfu/g) | 8.2 × 10$^5$ | 1.1 × 10$^4$ | 6.6 × 10$^3$ | 300 or less |

TABLE 1-continued

|  |  | Initial bacterial count | Bacteria sterilization | count | after |
|---|---|---|---|---|---|
| Fungi count (cfu/g) |  | 3.5 × 10$^5$ | 5.3 × 10$^5$ | 1.1 × 10$^2$ | 1.1 × 10$^2$ |
| Sterilization rate (%) | General live bacteria | — | 96.6 | 99.2 | about 100 |
|  | Fungi | — | 94.9 | 99.7 | 99.97 |

As can be seen from Table 1, it is possible to obtain a higher sterilization rate under a higher humidity condition.

Figure 3:
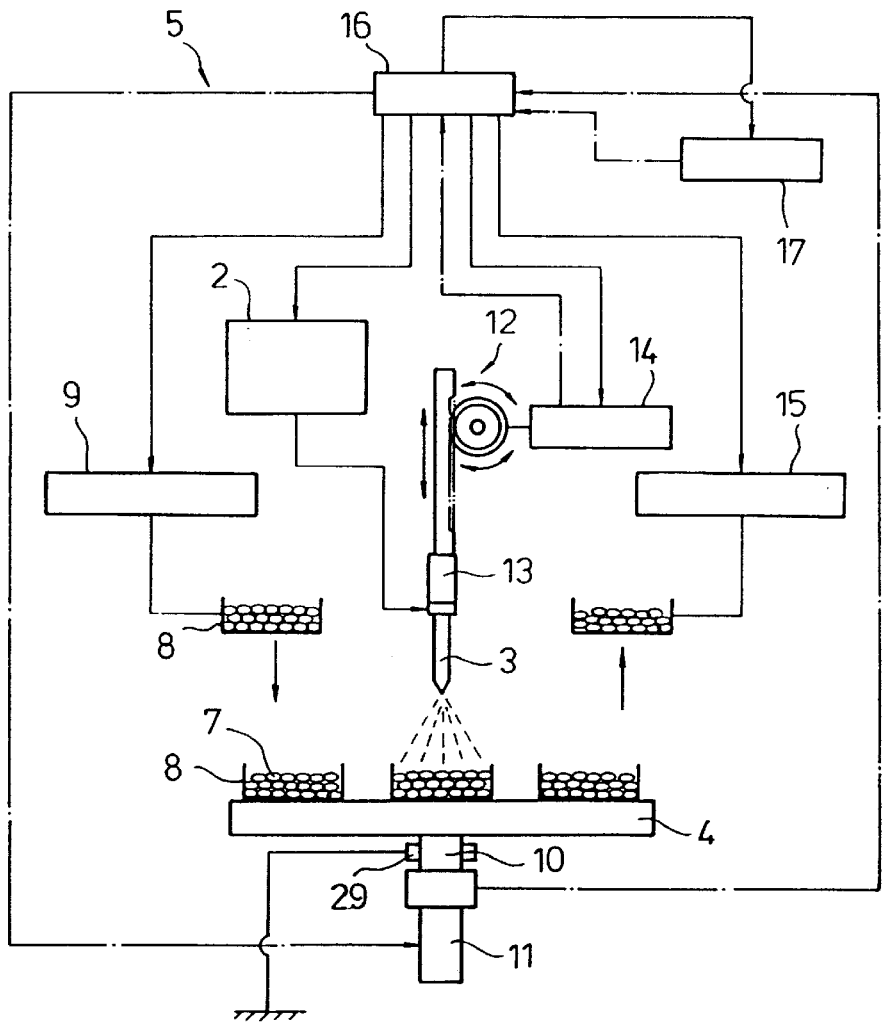
FIG. 3 is a diagram showing a general structure of another sterilizer of the present invention which utilizes a high voltage.

FIG. 3 is a diagram showing a general structure of a sterilizer utilizing a high voltage according to another embodiment of the present invention. In FIG. 3, the processing device 5 of the sterilizer of the present invention comprises a power supply section 2 for generating a high voltage, and a discharge side electrode 3 and a ground side electrode 4 to which the generated high voltage is applied. A predetermined amount of the sterilization objects 7 is contained in an insulating container 8 (e.g., polyethylene Schale container), and placed on the ground side electrode 4 by a manipulator 9. The manipulator 9 grabs the insulating container 8 containing the sterilization objects 7 therein from the previous step, and places the insulating container 8 on the ground side electrode 4.

Figure 4:
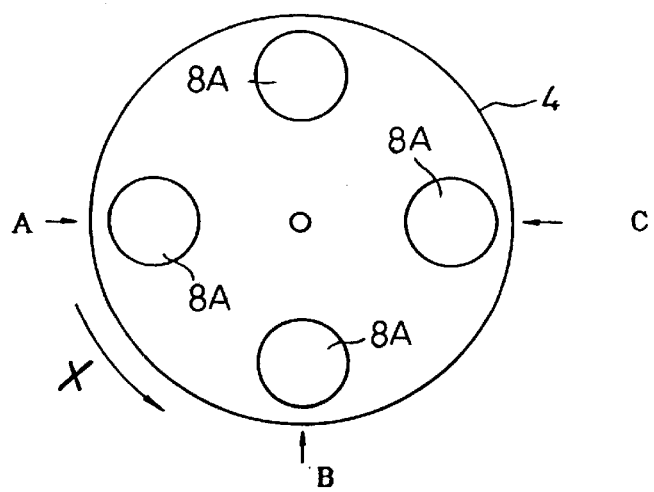
FIG. 4 is a plan view showing a turn table of the sterilizer of the present invention shown in FIG. 3 when viewed from the above.

FIG. 4 illustrates positions 8A at which the insulating container 8 is disposed on the ground side electrode 4. The ground side electrode 4 is a circular turn table, and FIG. 4 is a plan view of the turn table when viewed from the above. As shown in FIG. 4, four positions 8A are provided at even intervals in the circumferential direction with respect to a rotation axis 10 of the turn table of the ground side electrode 4. The rotation of a motor 11 causes the turn table to intermittently transfer the insulating container 8 containing the sterilization objects 7 therein, which has been placed at a position A by the manipulator 9 in a direction shown by an arrow X for every rotation angle of 90°.

The rotation axis 10 of the above-described turn table which is the ground side electrode 4 and the rotation axis 10 of the motor 11 are electrically connected with each other. The rotation axis 10 is rotatably grounded by the ground means 29 of a sliding brush.

As shown in FIG. 3, the discharge side electrode 3 which is fixed to lift means 12 including, for example, a pinion-rack mechanism via an insulating member 13 is provided above a position B. The discharge side electrode 3 is vertically moved by the driving of driving means 14. The discharge side electrode 3 is connected to the power supply section 2 for generating a high AC voltage or a pulsed high voltage.

A manipulator 15 grabs the insulating container 8 which has been transferred by the rotation of the turn table which is the ground side electrode 4, and transfers the insulating container 8 to the next step, e.g., the step of placing the sterilization objects 7 which have been sterilized in a predetermined container (not shown).

The above-described motor 11 includes a position detecting sensor (not shown) for detecting the rotation angle thereof. Control means 16 controls the operations of the motor 11, the manipulators 9 and 15, and the driving means 14 respectively based on an output signal of the position detecting sensor. A position sensor (not shown) for detecting a vertical movement of the discharge side electrode 3 is provided in the driving means 14. The control means 16 controls turning ON/OFF of the power supply section 2 based on an output signal of the position sensor.

There is also provided humidity control means 17 for controlling a humidity in the processing tank 5. The control means 16 transmits a signal to the humidity control means 17 based on an output signal of a humidity sensor (not shown) so as to actuate the humidity control means 17, thereby controlling the humidity of the atmosphere in the processing tank 5 to be a predetermined humidity suitable for sterilization.

Next, the operation of the above-described sterilizer will be described in detail. First, when a start button is operated to start the operation of the sterilizer, the control means 16 drives the manipulator 9 so as to place the insulating container 8 containing the sterilization objects 7 therein on the turn table which is the ground side electrode 4 at the position A. When the container 8 is placed on the turn table, the control means 16 drives the motor 11 so as to transfer the container 8 to the position B (90° as a rotation angle of the turn table).

When the container 8 is stopped at the position B, the control means 16 controls the driving means 14 so as to drive the lift means 12, thereby lowering the discharge side electrode 3 to be adjacent to the sterilization objects 7 in the container 8. If it is detected that the discharge side electrode 3 is placed at a predetermined position so as to be adjacent to the sterilization objects 7 in the container 8, the power supply section 2 is turned "ON" so as to apply a high voltage to the discharge side electrode 3 Based on an output signal of the humidity sensor (not shown), the control means 16 transmits a signal to the humidity control means 17 so as to actuate the humidity control means 17, thereby controlling the humidity of the atmosphere in the processing tank 5 to be a predetermined humidity suitable for sterilization, e.g., 50% RH.

Consequently, since the turn table which is the ground side electrode 4 is grounded, a pulse streamer discharge occurs between the discharge side electrode 3 and the turn table which is the ground side electrode 4 opposing to the discharge side electrode 3 via the container 8. Ions or electrons irradiated by the pulse streamer discharge sterilize the sterilization objects 7 in the container 8.

Next, when the pulse streamer discharge stops, the control means 16 controls the driving means 14 so as to drive the lift means 12, thereby raising the discharge side electrode 3 to be apart from the container 8. When the position sensor (not shown) provided in the driving means 14 detects that the discharge side electrode 3 is apart from the container 8, the motor 11 is driven so as to transfer the container 8 to a position C. Thereafter, when it is detected that the container 8 is stopped at the position C, the manipulator 15 is driven so as to grab the container 8 for transferring it to the next step, e.g., placing the sterilization objects 7 which have been sterilized in the container 8 into a predetermined container (not shown).

When the container 8 is stopped at the position B, the control means 16 drives the manipulator 9 at the position A So as to place the next container 8 containing the sterilization objects 7 therein on the turn table. Therefore, the container 8 is successively transferred to the position B to be subjected to sterilization by a pulse streamer discharge.

Figure 5:
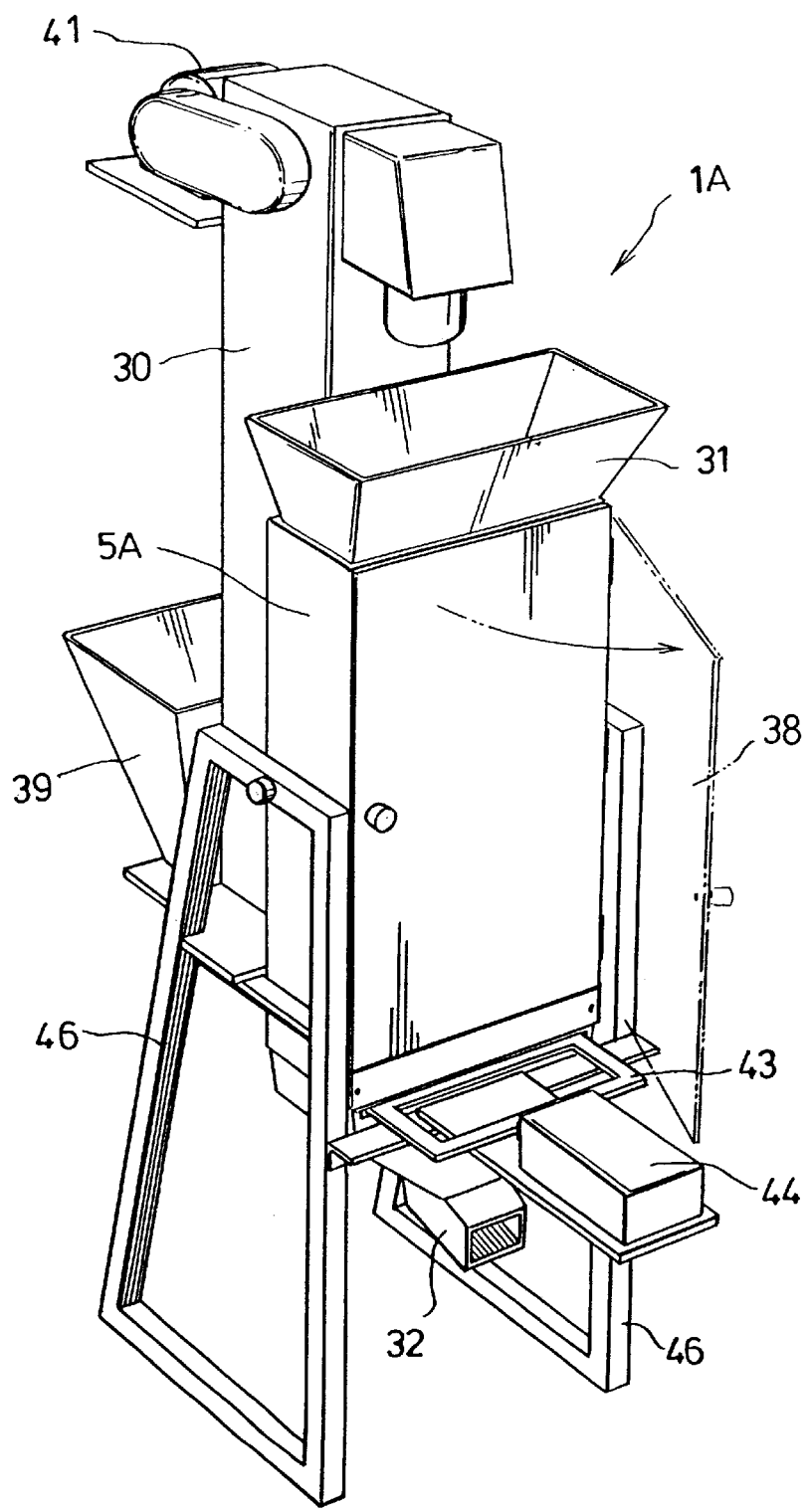
FIG. 5 is a diagram showing a general structure of a sterilizer utilizing a high voltage according to another embodiment of the present invention.
Figure 6:
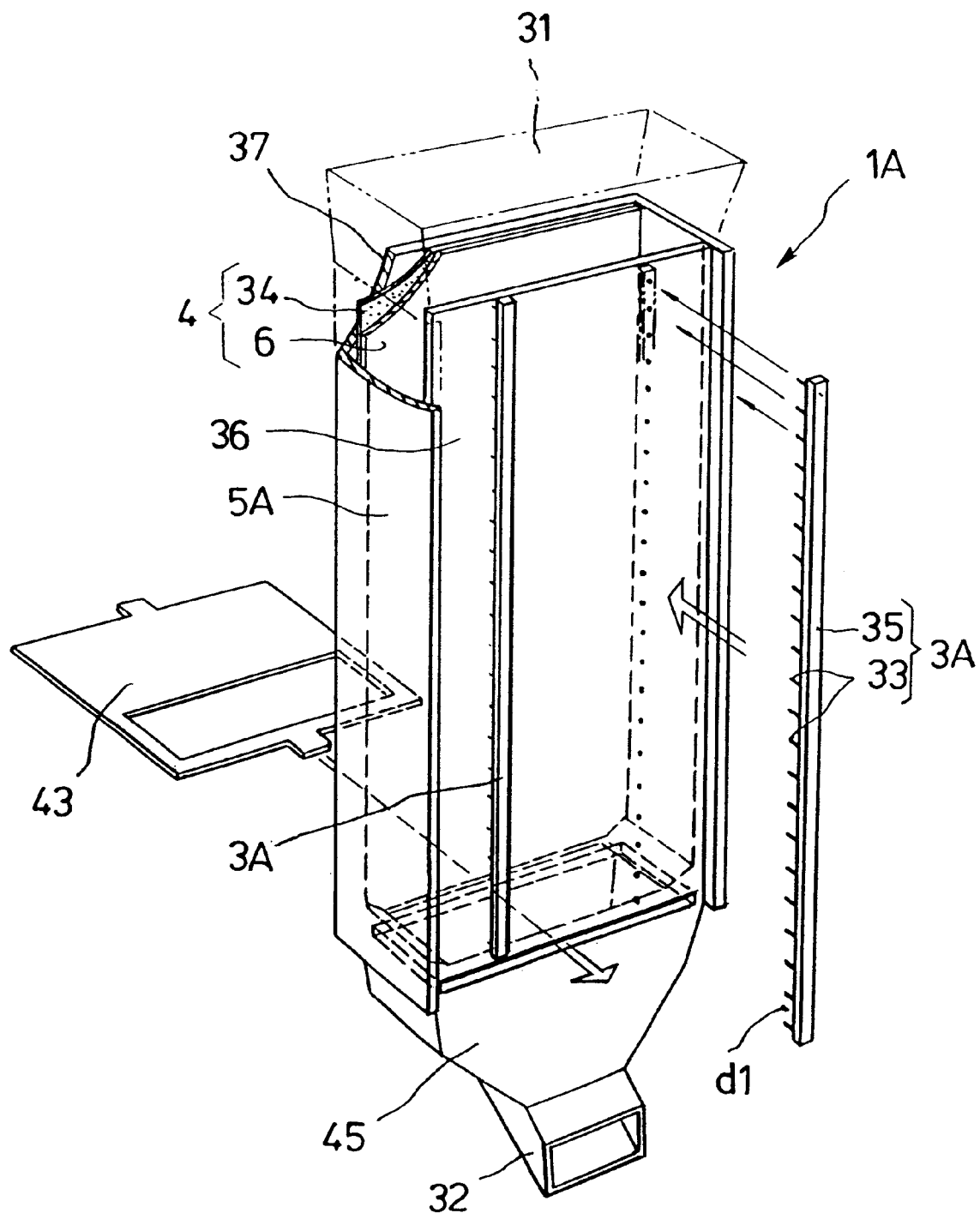
FIG. 6 is a diagram for illustrating a discharge side electrode, a ground side electrode, and a shutter capable of being opened and closed which is provided in a lower part thereof in the sterilizer shown in FIG. 5.
Figure 7:
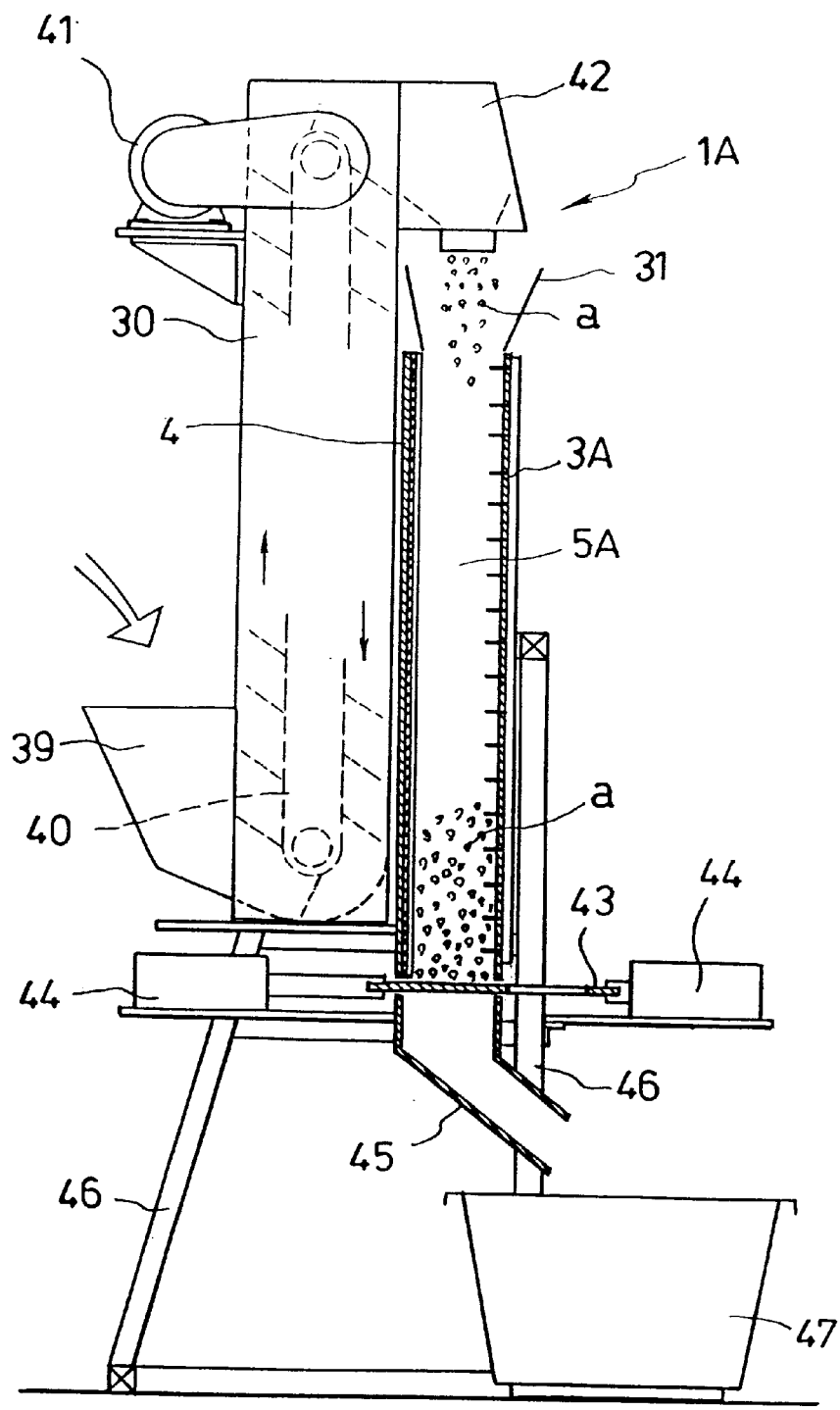
FIG. 7 is a side view of the sterilizer shown in FIG. 5 which is partially shown in cross section.
Figure 8:
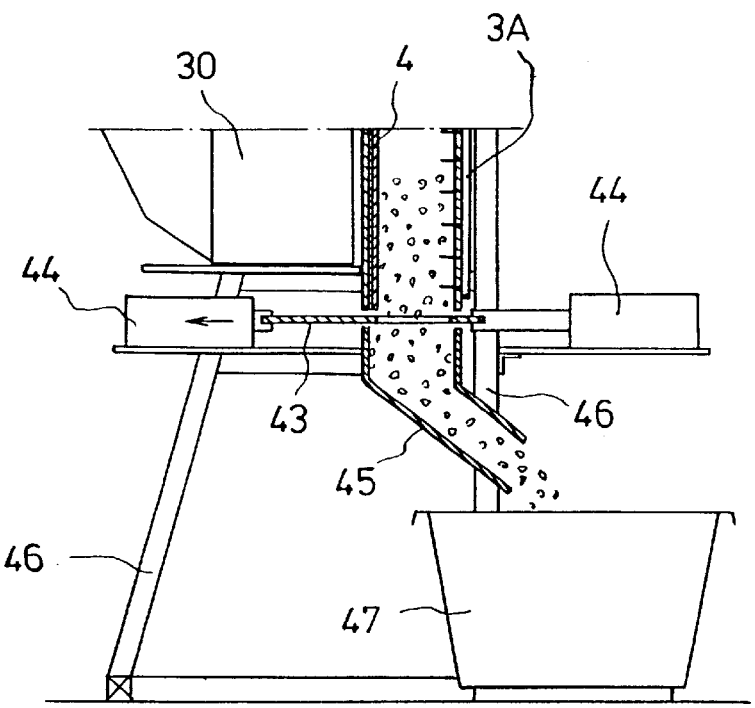
FIG. 8 is a diagram for illustrating a state in which sterilization objects which have been sterilized are discharged to the outside by opening the shutter provided at the lower part of the sterilizer shown in FIG. 5 which is capable of being opened and closed.
Figure 9:
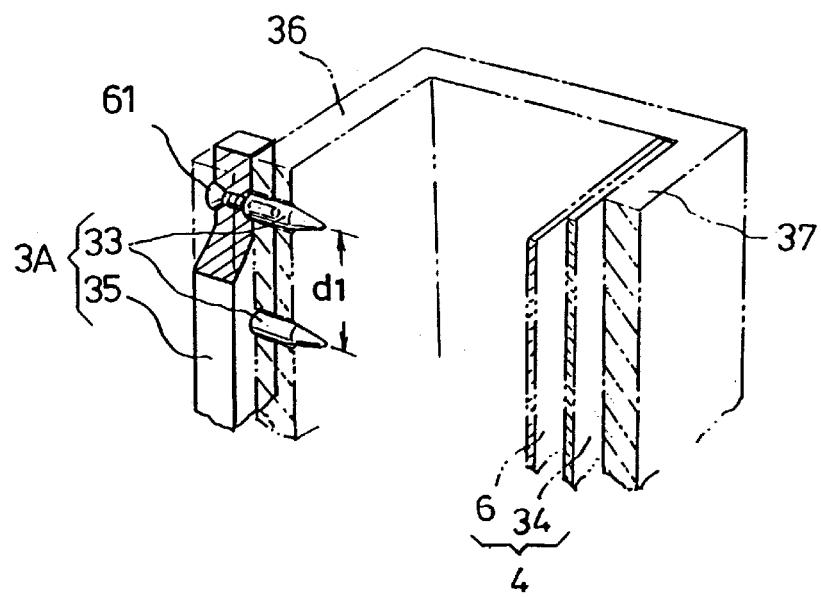
FIG. 9 is a diagram for illustrating the discharge side electrode and the ground side electrode of the sterilizer shown in FIG. 5.
Figure 10:
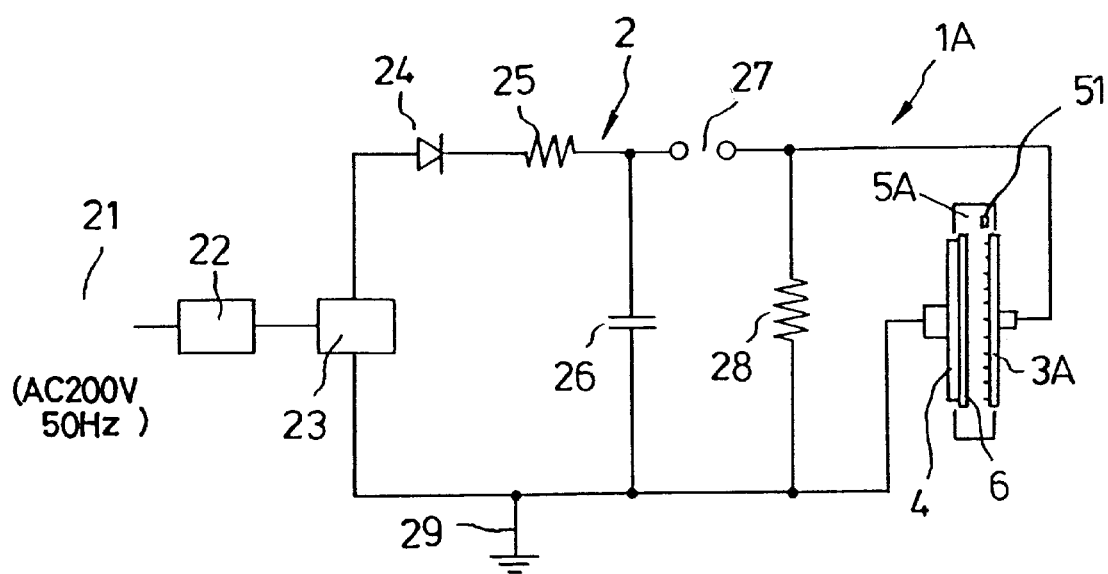
FIG. 10 is a diagram for illustrating an example of a power supply used in the sterilizer shown in FIG. 5.

FIG. 5 is a diagram showing a general structure of a sterilizer utilizing a high voltage according to another embodiment of the present invention FIG. 6 is a diagram for illustrating a discharge side electrode, a ground side electrode, and a shutter capable of being opened and closed which is provided in a lower part thereof in the sterilizer shown in FIG. 5. FIG. 7 is a side view of the sterilizer shown in FIG. 5 which is partially shown in cross section. FIG. 8 is a diagram for illustrating a state in which sterilization objects which have been sterilized are discharged from the sterilizer by opening the shutter provided at the lower part of the sterilizer shown in FIG. 5 which is capable of being opened and closed. FIG. 9 is a diagram for illustrating the discharge side electrode and the ground side electrode of the sterilizer shown in FIG. 5. FIG. 10 is a diagram for illustrating an example of a power supply used in the sterilizer shown in FIG. 5.

In FIGS. 5 through 10, the same components as those in the sterilizer of the present invention shown in FIGS. 1 through 4 are denoted by the same reference numerals as those used in the above-described sterilizer in order to eliminate duplicated explanation.

The case where unpolished rice is sterilized as a sterilization object will be described with reference to FIGS. 5 through 10

A sterilizer 1A of the present invention which utilizes a high voltage comprises: supply means 30 for supplying unpolished rice a; a hopper section 31 for storing the unpolished rice a which is supplied by the supply means 30; a processing device 5A for transferring the unpolished rice a which is stored in the hopper section 31 and sterilizing the unpolished rice a (the processing device 5A may be preferably made of an electrical insulating material such as an acrylic resin, a polycarbonate resin, or a FRP having a volume resistivity in the range of $10^{10}$~$10^{14}\Omega\cdot$cm or more); and discharge means 32 for discharging the unpolished rice a which has been sterilized in the processing device 5A to the outside of the processing device 5A. The sterilizer 1A actuates the humidity control means 51 (not shown) so as to control the atmosphere in the processing device 5A to have a humidity suitable for sterilization.

Discharge side electrodes 3A each including a large number of needle-shaped electrodes 33 which are disposed with a predetermined distance d1 apart from one another, and the ground side electrode 4 including a plate-shaped electrode 34 whose entire surface is covered with the insulating plate 6 (a ceramic plate) are provided in the processing device 5A.

Two discharge side electrodes 3A whose large number of needle-shaped electrodes 33 are firmly fixed to a conductor 35 (the conductor 35 may be preferably made of a stainless material as is the case with the needle-shaped electrode 33) via a vis 61 (the vis 61 may be preferably made of a stainless material as is the case with the needle-shaped electrode 33) are fixed to a front wall 36 of the processing device 5A so that the needle-shaped electrodes 33 are protruded from the inner surface of the processing device 5A.

The ground side electrode 4 is fixed to a rear wall 37 of the processing device 5A so that the plate-shaped electrode 34 whose entire surface is covered with the insulating plate 6 maintains a predetermined distance from the discharge side electrode 3A (the distance is generally in the range of about 10 mm to 50 mm, although the distance is not limited thereto) while being opposed to the discharge side electrode 3A inside of the processing device 5A. Reference numeral 38 denotes a door capable of being opened and closed, which is provided at the front side of the processing device 5A for safety.

The present invention requires the large number of needle-shaped electrodes 33 to be disposed with a predetermined constant distance d1 apart from one another. In the case where one needle-shaped electrode is used instead of using the large number of needle-shaped electrodes, wide-ranging sterilization of the unpolished rice a interposed between the above-described electrodes cannot be realized, resulting in uneven sterilization.

The distance d1 is not limited to any particular value since the applied voltage, pulse number, input energy (cal/cm$^3$), electric field strength, and the like are varied depending on the kind and form of the unpolished rice a, the kind and form of a bacterium, and the like. It is preferable that they are suitably determined so that the unpolished rice can be sufficiently and uniformly sterilized without deteriorating the qualities of a flavor, a taste, and the like, which are inherent to the unpolished rice.

However, it is desirable to select the distance d1 between two adjacent electrodes of the large number of needle-shaped electrodes 33 generally from the range of 5 mm to less than 80 mm, preferably from the range of 10 mm to 60 mm, and most preferably from the range of 25 mm to 30 mm. If the distance d1 is less than 5 mm, it is possible to sterilize unpolished rice. However, the capacity of the power supply section 2 needs to be increased, and thus, such a distance selection is uneconomical. If the distance d1 is 80 mm or more, wide-ranging and uniform sterilization of the unpolished rice a which is interposed between the above-described electrodes cannot be achieved, resulting in uneven sterilization.

The supply means 30, the hopper section 31, the processing device 5A, the discharge means 32, and the like are integrally connected to one another. The unpolished rice a supplied by the supply means 30 is stored in the hopper section 31. A predetermined amount of the unpolished rice a stored in the hopper section 31 is naturally dropped by gravity, thereby transferring the unpolished rice a so as to be interposed between the above-described electrodes 3A and 4 of the processing device 5A. A high voltage generated in the power supply section 2 is applied between the above-described electrodes 3A and 4, thereby causing a pulse streamer discharge between the electrodes 3A and 4. In this manner, the unpolished rice a is sterilized.

The supply means 30 comprises a supply port 39 for supplying the unpolished rice a, a conveyer 40, a motor 41 for driving the conveyer 40, a discharge port 42 for discharging the unpolished rice a which has been transferred by the conveyer 40 into the hopper section 31, and the like. As shown in FIG. 7, the unpolished rice a supplied into the supply port 39 in a direction indicated by a white arrow is transferred upwardly by means of the conveyer 40 which is driven by the motor 41, and supplied to the hopper section 31 via the discharge port 42.

The unpolished rice a which has been sterilized in the processing device 5A is naturally dropped and discharged to the outside of the processing device 5A by opening a shutter 43 capable of being opened and closed which is provided at a lower part of the processing device 5A.

The discharge means 32 comprises the shutter 43, a driving device 44 for opening and closing the shutter 43 (the driving device may be an electric driving device, a pneumatic driving device, or the like, having a solenoid valve), a discharge duct 45, and the like. Reference numeral 46 denotes a supporting device for supporting and securing the sterilizer 1A of the present invention, and reference numeral 47 denotes a container for receiving the unpolished rice a which has been sterilized.

When unpolished rice is sterilized using the sterilizer 1A of the present invention, sufficient control, e.g., performing a sterilization process in a sterile room, is necessary in order to prevent the unpolished rice a which has been sterilized from being contaminated again.

As shown in FIG. 10, by causing a pulse streamer discharge between the discharge side electrodes 3A and the ground side electrode 4 of the sterilizer 1A, the unpolished rice a interposed between the above-described electrodes 3A and 4 is sterilized at a room temperature and an atmospheric pressure and in the atmosphere in which a humidity is controlled.

In the present invention, the insulating plate 6 may be a sinqle piece of plate, or may be a plate formed by binding edges of small ceramic plates (e.g., $Al_2O_3$) with one another.

In the case where the insulating plate formed by binding the edges of many small ceramic plates (e.g., $Al_2O_3$) with one another is used as the insulating plate 6, it is preferable that the large number of needle-shaped electrodes 33 and junctions of the edges of the many ceramic plates have a certain relative positional relationship.

Specifically, it is preferred that the distance between the junction at an edge of a ceramic plate and the intersection between the ceramic plate and a straight line which extends from a needle-shaped electrode 33 in a direction perpendicular to the plate-shaped electrode 34 is 10 mm or more for any combination of a given one of such intersections and a given one of such junctions. If this distance is within about 5 mm, a discharge would certainly be shorted from the needle-shaped electrode 33 to the junction. If this distance is about 7 to 8 mm, a discharge may be shorted from the needle-shaped electrode 33 to the junction depending upon the applied voltage.

Sterilization conditions such as a sterilization processing time in the processing device 5A, a processing amount of the unpolished rice a, and a humidity are varied depending on the kind and form of the unpolished rice a, the kind and form of a bacterium, and the like. Therefore, it is preferable that sterilization conditions are suitably determined, and they are not limited to any particular conditions.

The sterilizer 1A of the present invention is actuated, and unpolished rice a supplied by the supply means 30 is stored in the hopper section 31. The unpolished rice a stored in the hopper section 31 is transferred so as to be interposed in a predetermined amount between the electrodes 3A and 4 of the processing device 5A in which the shutter 43 is closed. A high voltage generated in the power supply section 2 is applied between the electrodes 3A and 4, thereby causing a pulse streamer discharge between the electrodes 3A and 4. By placing the unpolished rice a under the sterilization condition, the unpolished rice a is sterilized. The unpolished rice a which has been sterilized in the processing device 5A is discharged to the outside of the processing device 5A by opening the shutter 43. By repeating the above-described operations, the unpolished rice a can be uniformly, efficiently and easily sterilized at a room temperature and an atmospheric pressure and in the atmosphere in which a humidity is controlled without deteriorating the quality of the unpolished rice a.

FIG. 11 is a diagram for illustrating another example of a shutter capable of being opened and closed which is provided at a lower part of the processing device 5A. FIG. 12A is a diagram for illustrating a state in which the shutter shown in FIG. 11 is closed, and FIG. 12B is a diagram for illustrating a state in which the shutter shown in FIG. 11 is opened.

In FIGS. 11, 12A, and 12B, components structurally same as those in FIGS. 1 through 10 and components having the same names as those in FIGS. 1 through 10 are denoted by the same reference numerals as those in FIGS. 1 through 10.

In FIGS. 11, 12A, and 12B, a shutter 43A is provided at a lower part of the processing device 5A. The shutter 43A is driven by an opening/closing device 48 such as a motor connected to the shutter 43A so as to be rotated to be opened or closed.

As shown in FIG. 12A, a predetermined amount of unpolished rice a is interposed between the electrodes 3A and 4 of the processing device 5A in which the shutter 43A is closed, and a high voltage generated in the power supply section 2 is applied between the electrodes 3A and 4, thereby causing a pulse streamer discharge between the electrodes 3A and 4 as described above. By placing the unpolished rice a under the sterilization condition so as to be subjected to sterilization, the unpolished rice a which has been sterilized is discharged to the outside of the processing device 5A as shown in FIG. 12B by opening the shutter 43A using the opening/closing device 48 as indicated by a white arrow.

Each of FIGS. 13A and 13B is a diagram for illustrating the sterilizer in which shutters capable of being opened and closed are respectively provided at a lower part of the hopper section and a lower part of the processing device. FIG. 13A is a diagram for illustrating a state in which unpolished rice in the hopper section is transferred to a processing tank by closing the shutter provided at the lower part of the sterilizer and opening the shutter provided at the lower part of the hopper section. FIG. 13B is a diagram for illustrating a state in which unpolished rice which has been sterilized is discharged by opening the shutter provided at the lower part of the processing device.

In FIGS. 13A and 13B, components structurally same as those in FIGS. 1 through 12 and components having the same names as those in FIGS. 1 through 12 are denoted by the same reference numerals as those in FIGS. 1 through 12.

In each of FIGS. 13A and 13B, the shutters 43 which are opened and closed by the driving device 44 are provided at the lower parts of the hopper section 31 and the processing device 5A, respectively. As shown in FIG. 13A, the shutter 43 provided at the lower part of the processing device 5A is closed and the shutter 43 provided at the lower part of the hopper section 31 is opened so that a predetermined amount of the unpolished rice a among the unpolished rice a which has been temporarily stored in the hopper section 31 is transferred to be interposed between the electrodes 3A and 4. As described above, a high voltage generated at the power supply section 2 is applied between the electrodes 3A and 4, thereby causing a pulse streamer discharge between the electrodes 3A and 4. By placing the unpolished rice a under the sterilization condition so as to be subjected to sterilization, the unpolished rice a which has been sterilized is discharged to the outside by opening the shutter 43 which is provided at the lower part of the processing device 5A by means of the driving device 44 as indicated by a white arrow shown in FIG. 13B. The humidity control means 51 (not shown) is actuated so as to control the atmosphere in the processing device 5A to have a humidity suitable for sterilization FIG. 14 is a perspective view showing another example of a sterilizer of the present invention which utilizes a high voltage.

Figure 14:
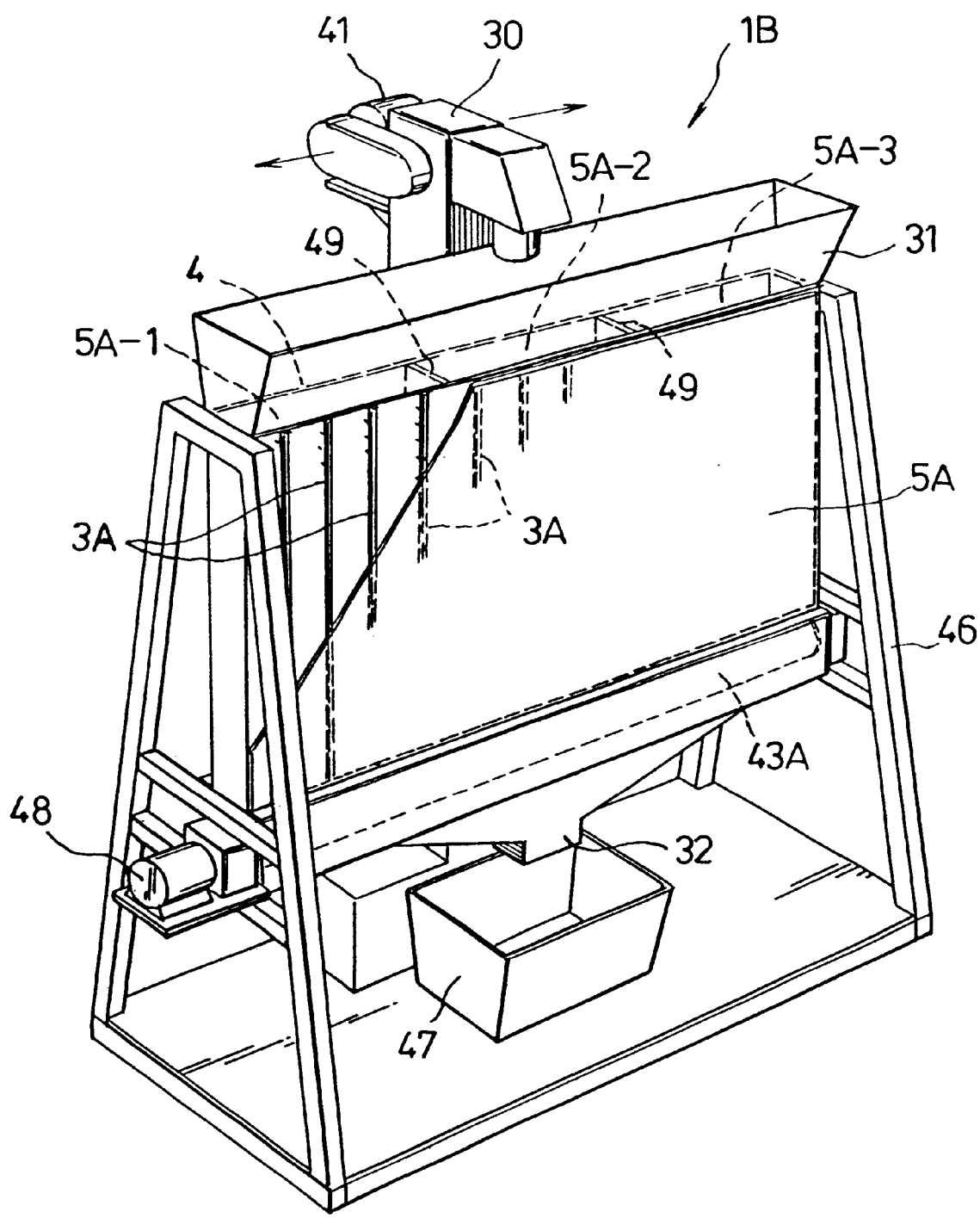
FIG. 14 is a perspective view showing another example of a sterilizer of the present invention which utilizes a high voltage.

In FIG. 14, components structurally same as those in FIGS. 1 through 13 and components having the same names as those in FIGS. 1 through 13 are denoted by the same reference numerals as those in FIGS. 1 through 13.

A sterilizer 1B of the present invention shown in FIG. 14 is an enlarged version of the sterilizer 1A of the present invention shown in FIGS. 5 through 9. Within the processing device 5A, there are three cells 5A-1, 5A-2, and 5A-3 which are separated by two separators 49 (the separators may be preferably made of an electrical insulating material such as an acrylic resin, a polycarbonate resin, or a FRP). A plurality of discharge side electrodes 3A and the ground side electrode 4 are provided in the respective cells. The shutter 43A, which is driven by the opening/closing device 48 such as a motor so as to be rotated to be opened or closed, is provided at the lower part of the processing device 5A. The sterilizer 1B is identical to the sterilizer 1A of the present invention shown in FIGS. 5 through 9 except that the supply means 30 is driven by a driving device (not shown) so that it can move in a horizontal direction as shown by arrows in FIG. 14 along the hopper section 31 in order to transfer a predetermined amount of unpolished rice a respectively to the cells 5A-1, 5A-2, and 5A-3 from the hopper section 31. The sterilizer 1B of the present invention actuates the humidity control means 51 (not shown) so as to control the atmosphere in the processing device 5A to have a humidity suitable for sterilization.

The sterilizer 1B of the present invention is actuated and the supply means 30 is moved in a horizontal direction along the hopper section 31, thereby storing unpolished rice a supplied by the supply means 30 in the hopper section 31. A predetermined amount of the unpolished rice a which has been stored in the hopper section 31 is transferred so that a predetermined amount of the unpolished rice a is interposed between the electrodes 3A and 4 in each of the cells 5A-1, 5A-2, and 5A-3 in which the shutter 43A is closed. As described above, a high voltage generated at the power supply section 2 is applied between the electrodes 3A and 4, thereby causing a pulse streamer discharge therebetween. By placing the unpolished rice a under the sterilization condition, it is possible to sterilize a large amount of unpolished rice a. The unpolished rice a which has been sterilized is discharged to the outside by opening the shutter 43A. By repeating the above-described operations, a large amount of unpolished rice a can be uniformly, efficiently and easily sterilized at a room temperature and an atmospheric pressure and in the atmosphere in which a humidity is controlled without deteriorating the qualities of the large amount of unpolished rice a.

While the presently preferred embodiments of the present invention have been shown and described, it will be understood that the present invention is not limited thereto, and that various changes and modifications may be made by those skilled in the art without departing from the scope of the invention as set forth in the appended claims.

⊠1

21 power supply

⊠3

16 control means 17 humidity control means 14 driving means 9, 15 manipulator 2 power supply section for generating a high voltage

⊠4 position A position B position C

⊠10

21 power supply section

What is claimed is:

1. A sterilizer utilizing a high voltage, comprising:

a power supply section for generating a high voltage;

a processing device having a discharge side electrode and a ground side electrode to which the generated high voltage is applied; and a humidity control means which controls humidity in the processing device by the use of a humidity sensor, wherein a sterilization object selected from the group consisting of a food, a drug, a Chinese herb medicine, a cosmetic, and a fertilizer is interposed between the electrodes of the processing device, and a pulse streamer discharge occurs between the electrodes, and wherein the discharge side electrode comprises a large number of needle-shaped electrodes which are provided with a predetermined distance apart from one another.

2. The sterilizer according to claim 1, wherein the ground side electrode comprises a plate-shaped electrode whose entire surface is covered with an insulating plate.

3. The sterilizer according to claim 2, wherein the insulating plate is a ceramic plate.

4. The sterilizer according to claim 3, wherein the ceramic plate is a ceramic plate having a high withstand voltage.

5. In a processing device having a discharge side electrode and a ground side electrode to which a high voltage generated in a power supply section for generating a high voltage is to be applied, a sterilization method, comprising the steps of:

interposing a sterilization object selected from the group consisting of a food, a drug, a Chinese herb medicine, a cosmetic, and a fertilizer between the electrodes to which a high voltage is applied, and causing a pulse streamer discharge between the electrodes at a room temperature and an atmospheric pressure and in the atmosphere in which humidity is controlled by the use of a humidity sensor to be suitable for the sterilization, thereby performing sterilization, wherein the discharge side electrode comprises a large number of needle-shaped electrodes which are provided with a predetermined distance apart from one another.

6. The sterilization method according to claim 5, wherein a pulsed high voltage of a positive polarity is applied to the discharge side electrode.

7. The sterilization method according to claim 5, wherein a pulsed high voltage with a start-up time of 10 nanoseconds or more and a duration of 1 microsecond or less is applied to the discharge side electrode.

8. The sterilization method according to claim 6, wherein a pulsed high voltage with a start-up time of 10 nanoseconds or more and a duration of 1 microsecond or less is applied to the discharge side electrode.

* * * * *

UNITED STATES PATENT AND TRADEMARK OFFICE
CERTIFICATE OF CORRECTION

PATENT NO. : 6,497,839 B1 Page 1 of 1
DATED : December 24, 2002
INVENTOR(S) : Hideo Hasegawa et al.

It is certified that error appears in the above-identified patent and that said Letters Patent is hereby corrected as shown below:

Column 8,
Table 1, "$1.1 \times 10^2$" (first occurrence) should read -- $1.1 \times 10^3$ --; and Column 12,
Line 12, "sinqle" should read -- single --.

Signed and Sealed this

Fourth Day of May, 2004

JON W. DUDAS
*Acting Director of the United States Patent and Trademark Office*